(12) United States Patent
Schmidberger et al.

(10) Patent No.: US 7,857,784 B2
(45) Date of Patent: Dec. 28, 2010

(54) MEDICAL INSTRUMENT FOR SUCTION AND IRRIGATION, AND METHOD FOR ITS PRODUCTION

(75) Inventors: Jochen Schmidberger, Schoerzingen (DE); Andreas Efinger, Rietheim (DE)

(73) Assignee: Karl Storz GmbH & Co. KG (DE)

( * ) Notice: Subject to any disclaimer, the term of this patent is extended or adjusted under 35 U.S.C. 154(b) by 1118 days.

(21) Appl. No.: 11/083,536

(22) Filed: Mar. 18, 2005

(65) Prior Publication Data
US 2005/0182353 A1 Aug. 18, 2005

Related U.S. Application Data

(63) Continuation of application No. PCT/EP2003/009025, filed on Aug. 14, 2003.

(30) Foreign Application Priority Data
Sep. 20, 2002 (DE) .................... 102 45 009

(51) Int. Cl.
*A61M 3/00* (2006.01)
(52) U.S. Cl. .............. 604/43; 604/45; 604/102.03; 604/118; 604/164.13; 604/170.02; 604/173; 604/191; 604/509; 604/95.03; 604/96.01; 604/101.01; 600/563; 600/115; 600/116
(58) Field of Classification Search ................. 600/563, 600/115, 116; 604/43, 45, 102.03, 118, 164.13, 604/170.02, 173, 191, 509, 95.03, 96.01, 604/101.01
See application file for complete search history.

(56) References Cited
U.S. PATENT DOCUMENTS

| | | | | |
|---|---|---|---|---|
| 3,788,326 A | * | 1/1974 | Jacobs | 128/207.15 |
| 4,316,941 A | * | 2/1982 | Eguchi et al. | 428/421 |
| 4,607,635 A | * | 8/1986 | Heyden | 128/207.15 |
| 4,619,643 A | * | 10/1986 | Bai | 604/43 |
| 4,732,139 A | | 3/1988 | Kawashima et al. | |
| 4,840,173 A | * | 6/1989 | Porter, III | 128/207.15 |
| 5,146,916 A | * | 9/1992 | Catalani | 128/207.14 |

(Continued)

FOREIGN PATENT DOCUMENTS

DE 36 29 858 A1 4/1987

(Continued)

OTHER PUBLICATIONS

Saug- und Spuelrohre, Karl Storz Endoscope, 1 page.

*Primary Examiner*—Nicholas D Lucchesi
*Assistant Examiner*—Scott Medway
(74) *Attorney, Agent, or Firm*—St. Onge Steward Johnston & Reens LLC

(57) ABSTRACT

A medical instrument for suction and irrigation comprises an elongate shaft with a first channel serving as suction channel and with a second channel serving as irrigation channel, the shaft having a first tube which is closed in cross section and in which one of the channels is present. The shaft has a second tube which is open in cross section along its length and is placed with its open lengthwise side on an outside face of the first tube and secured sealingly thereon, the other channel being formed in the space between the outside face of the first tube and an inside face of the second tube. A method for production of the instrument is also described.

17 Claims, 5 Drawing Sheets

U.S. PATENT DOCUMENTS

| | | | |
|---|---|---|---|
| 5,306,249 A * | 4/1994 | Don Michel | 604/101.05 |
| 5,336,178 A * | 8/1994 | Kaplan et al. | 604/509 |
| 5,374,245 A * | 12/1994 | Mahurkar | 604/43 |
| 5,378,230 A * | 1/1995 | Mahurkar | 604/43 |
| 5,380,276 A * | 1/1995 | Miller et al. | 604/28 |
| 5,487,339 A * | 1/1996 | Breventani et al. | 101/483 |
| 5,575,756 A | 11/1996 | Karasawa et al. | |
| 5,599,299 A * | 2/1997 | Weaver et al. | 604/540 |
| 5,672,171 A * | 9/1997 | Andrus et al. | 606/15 |
| 5,709,698 A * | 1/1998 | Adams et al. | 606/180 |
| 5,810,767 A * | 9/1998 | Klein | 604/509 |
| 5,810,776 A * | 9/1998 | Bacich et al. | 604/131 |
| 5,832,920 A * | 11/1998 | Field | 128/207.14 |
| 6,004,291 A * | 12/1999 | Ressemann et al. | 604/96.01 |
| 6,042,593 A | 3/2000 | Storz et al. | |
| 6,234,993 B1 | 5/2001 | Terpilowski et al. | |
| 6,814,718 B2 * | 11/2004 | McGuckin et al. | 604/264 |
| 2001/0037085 A1 * | 11/2001 | Keith et al. | 604/96.01 |
| 2002/0177800 A1 * | 11/2002 | Bagaoisan et al. | 604/6.12 |
| 2003/0163082 A1 * | 8/2003 | Mertens | 604/43 |
| 2006/0036132 A1 * | 2/2006 | Renner et al. | 600/160 |

FOREIGN PATENT DOCUMENTS

| | | |
|---|---|---|
| DE | 196 33 124 A1 | 5/1997 |
| DE | 102 45 009 A1 | 4/2004 |
| FR | 2 588 744 | 4/1987 |
| WO | WO 00/48505 | 8/2000 |

* cited by examiner

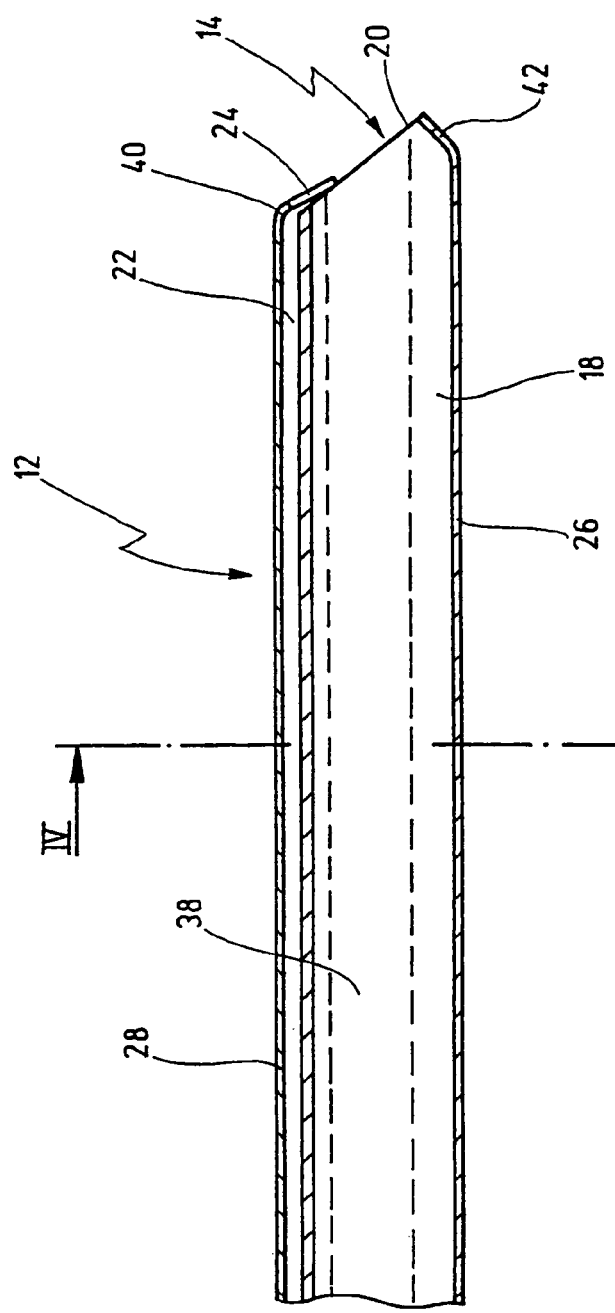
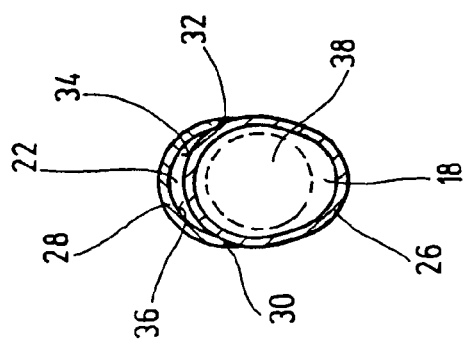
Fig.3
Fig.4

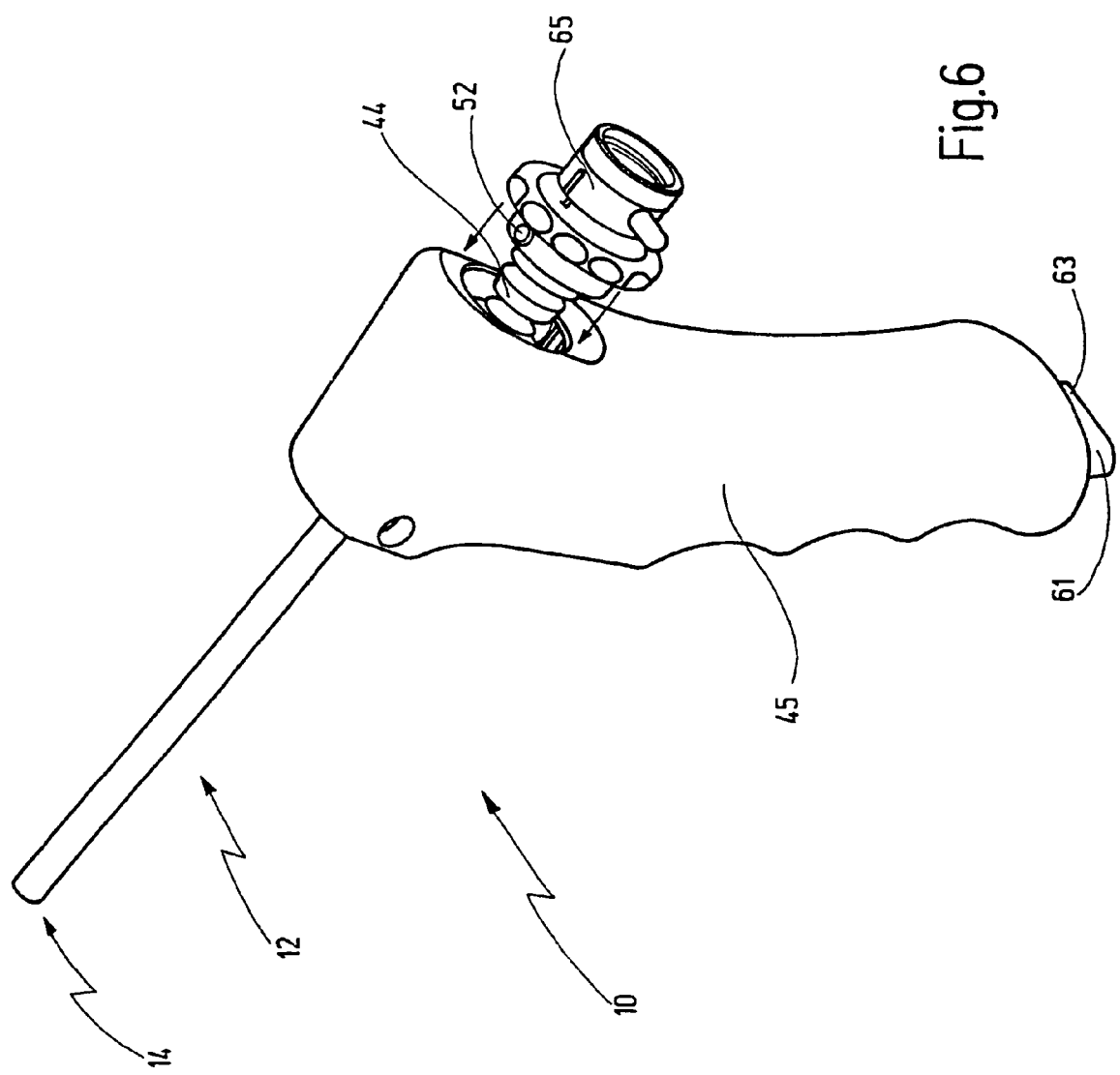

MEDICAL INSTRUMENT FOR SUCTION AND IRRIGATION, AND METHOD FOR ITS PRODUCTION

CROSS REFERENCE TO RELATED APPLICATIONS

The present application is a continuation of pending International patent application PCT/EP2003/009025 filed on Aug. 14, 2003 which designates the United States, and which claims priority of German patent application 102 45 009.9 filed on Sep. 20, 2002.

BACKGROUND OF THE INVENTION

The invention relates to a medical instrument for suction and irrigation, having an elongate shaft with one channel serving as suction channel and with another channel serving as irrigation channel.

The invention further relates to a method for producing such a medical instrument.

An instrument of the kind mentioned above is known from the company brochure produced by the German company Karl Storz GmbH & Co. KG, "STORZ Karl Storz-Endoskope", volume entitled "Laparoskopie", 3rd edition 2/99, page IS-ACC 5 A.

When performing surgical procedures on the human or animal body, such an instrument is used to irrigate the operating site with fresh irrigation fluid and to suction the irrigation fluid together with blood and tissue residues back out from the operating site. In endoscopic procedures, irrigation also serves to maintain a clear view through an endoscope.

To permit suction and irrigation simultaneously, it is necessary for such an instrument to have a shaft with two channels, specifically a suction channel and an irrigation channel. Since the fresh irrigation fluid should not mix with the suctioned fluid before reaching the operating site, it is also necessary for the irrigation channel to be separated from the suction channel so that irrigation fluid and suctioned fluid do not mix together in the shaft.

The shaft of the instrument known from the abovementioned German company brochure has a first tube for the irrigation channel and a second tube for the suction channel, in which the first tube forming the irrigation channel is pushed as an insert into the second tube forming the suction channel. The suction channel is accordingly formed between the outside face of the first tube forming the irrigation channel and the inside face of the second tube. The shaft of this instrument is thus composed of two tubes which are essentially not connected to one another, and this can lead to a number of disadvantages. On the one hand, individual tubes have less flexural stability, and, on the other hand, they each have to be individually sealed off from the outside by suitable sealing measures, for example O-ring seals, which are subject to wear. The arrangement of an irrigation tube and a suction tube inserted one inside the other also has the disadvantage that, in the suction tube and in the thin irrigation tube, there is no room for insertion of an endoscope, unless the cross section chosen for the whole shaft is of a considerable size, which is undesirable in the field of minimally invasive surgery performed through very small incisions in the body. In addition, the individual tubes have to be assembled before use of the instrument and disassembled before the instrument is cleaned, which makes handling of the instrument difficult.

Moreover, WO 00/48505 discloses an endoscope with an outer shaft in which a shaped shaft divided into chambers is arranged, with one chamber serving as irrigation channel and a separate, further chamber serving as suction channel. In the shaped shaft there is also an optical channel for receiving an optical system and further chambers for receiving a light-transmitting system, for example optical fibers. In this design, although the irrigation channel and the suction channel are integrally connected to one another, a shaped shaft of this kind is relatively complicated to produce since it can only be made in an extrusion process.

SUMMARY OF THE INVENTION

It is an object of the invention to improve a medical instrument of the type mentioned at the outset so that the shaft, while being easy to produce, has a compact cross section for a combined suction and irrigation channel.

A further object of the invention is to make available a method for producing such an instrument.

According to a first aspect of the invention, a medical instrument for suction and irrigation is provided, comprising an elongate shaft, said shaft having a first tube which is closed in cross section and in which a first channel is present, a second tube having a longitudinal open side extending over a length of said second tube, said second tube being placed and secured sealingly with said longitudinal open side on an outside face of said first tube, thus defining a space between said outside face of said first tube and an inside face of said second tube, said space defining a second channel of said shaft.

According to another aspect of the invention, a method for producing a medical instrument for suction and irrigation is provided, comprising providing a first tube which is closed in cross section and in which a first channel is present, providing a second tube having a longitudinal open side extending over a length of said second tube, placing and securing sealingly said second tube with said longitudinal open side on an outside face of said first tube, thus defining a space between said outside face of said first tube and an inside face of said second tube, said space defining a second channel of said shaft.

The instrument according to the invention differs from the instrument according to the prior art in that the shaft is not now formed by two individual tubes which can be inserted one into the other and then separated again from one another, and instead the shaft of the instrument according to the invention has, in order to form one of the two channels, a second tube which is open in cross section along its length and which is placed with its open lengthwise side on an outside face of the first tube and secured sealingly thereon. In this way, the second tube spans only part of the circumference of the first tube, which means that the overall cross section of the shaft is on the one hand kept small, and, on the other hand, there is the additional possibility of being able to insert an endoscope into the first tube since the interior of the first tube is now left free. The second tube placed on the first tube and connected fixedly thereto additionally increases the flexural strength of the overall arrangement of suction tube and irrigation tube. A further important advantage of the instrument according to the invention is that the access to the first tube and the access to the second tube for introducing and removing fluid does not have to take place through the respective other tube, because the second tube covers only part of the circumference of the outside face of the first tube, while the rest of the circumference of the first tube is left free. The production of the shaft of the instrument according to the invention is also greatly simplified since the second tube can be fixedly secured on the outside face of the first tube by simple connecting methods, for example adhesive bonding, soldering or welding.

In a further preferred embodiment, the space between the outside face of the first tube and the inside face of the second tube is designed in the shape of a crescent with a low height.

An advantage here is that the second tube increases the overall cross section of the shaft only slightly beyond the cross section of the first tube. The space of crescent-shaped cross section between the outside face of the first tube and the inside face of the second tube is especially suitable for the irrigation channel since the irrigation fluid does not contain any solid substances that can stick in the corners of the crescent-shaped cross section.

In a further preferred embodiment, the first tube also has a third channel for receiving an optical shaft of an endoscope, and the second tube is placed on that outside face of the first tube directed away from the remaining free cross section in the first tube which forms the first or second channel.

This arrangement of the second tube has the advantage that the irrigation fluid, on emerging from the distal end of one tube, is caused to flow past the distal end of the optical shaft because of the suction pressure at the distal end of the other tube, by which means it is possible to ensure that the view through the endoscope is not impeded by blood or by tissue residues.

In a further preferred embodiment, the second tube protrudes slightly in the longitudinal direction beyond the outside face of the first tube on which it is placed.

By this means, the above-described effect of the irrigation fluid flowing past the light-entrance end of the endoscope is still further improved.

In a further preferred embodiment, a distal end of the second tube is flanged in toward the first tube, and/or a distal end of the first tube, on the outside face directed away from the second tube, is flanged in toward said second tube.

These measures too advantageously contribute to improved flushing of the distal end of the optical shaft of the endoscope optionally introduced into the first tube, and the suction action of the instrument is also improved by this means.

In a further preferred embodiment, the suction channel is arranged in the first tube and the irrigation channel is arranged in the space between the outside face of the first tube and the inside face of the second tube.

Especially when, as in an above-described embodiment, the space between the inside face of the second tube and the outside face of the first tube is designed in the shape of a crescent with low height, this measure is especially advantageous because a smaller cross section is needed for the irrigation fluid than for the suctioned fluid which may also contain solid substances, in particular tissue residues, so that the cross section of the shaft with combined suction channel and irrigation channel can be kept small.

In a further preferred embodiment, the second tube along its lengthwise edges is fixedly connected to the outside face of the first tube by adhesive bonding, soldering or welding.

If the second tube has its lengthwise edges fixedly connected directly to the first tube, this has the advantage that no corners or niches in which impurities can gather are formed on the outside face of the first tube in the area of the connection to the second tube. In this way, the shaft of the instrument according to the invention is easy to clean. Any edges are filled in or smoothed over by the adhesive, the solder or the weld material.

It is especially preferred if the second tube along its lengthwise edges is connected to the outside face of the first tube by laser welding.

Connecting the second tube to the first tube by laser welding has the advantage that laser welding produces a very exact and thin weld seam which affords sufficient protection against corrosion and soiling at the connection point between the first tube and the second tube.

In a further preferred embodiment, a connection part surrounding the shaft and used to connect said shaft to a handgrip is arranged at the proximal end of the shaft, said shaft being bonded into the connection part by means of a curing adhesive.

An advantage of this is that not only the shaft as a whole is formed as one piece, but the arrangement composed of the shaft and of the connection part for connecting the shaft to a handgrip is also designed in one piece, which further simplifies the assembly and disassembly of the instrument. Connecting the shaft to the connection part by means of a curing adhesive has the advantage that this can be done in a way which is simple in terms of production technology and also inexpensive, and, in addition, the adhesive is able to fill any gaps between the connection part and the shaft and thus adequately seal the connection part to the outside face of the shaft without further measures, so that no impurities or the like can get in between the shaft and the connection part.

In this context, it is also preferred if the adhesive seals off the first tube and the second tube from one another in their proximal end area.

An advantage of this is that it is possible to entirely dispense with sealing measures, such as the provision of O-rings, for sealing the two tubes so that the irrigation fluid cannot mix with the suctioned fluid.

Regarding the method mentioned at the outset and intended for producing a medical instrument for suction and irrigation, of which instrument comprises an elongate shaft with a first channel serving as suction channel and with a second channel serving as irrigation channel, the shaft having a first tube in which one of the channels is arranged, the second object mentioned above is achieved by the fact that a second tube which is open in cross section along its length is placed with its open lengthwise side on an outside face of the first tube and is secured sealingly thereon in such a way that a space continuous in the longitudinal direction remains between the outside face of the first tube and the inside face of the second tube.

The production method according to the invention has the advantage that the instrument with combined suction channel and irrigation channel can be produced in a particularly straightforward way in which the second tube, open along a lengthwise side, simply has to be placed with its open lengthwise side on an outside face of the first tube and secured sealingly thereon.

It is preferable for the second tube to be fixedly connected to the first tube by adhesive bonding, soldering or welding.

These connection techniques are all simple and inexpensive to perform and they permit permanent, mechanically stable and tight securing of the second tube on the first tube.

It is particularly preferable for the second tube to be connected to the first tube by laser welding.

As has already been mentioned above, laser welding has the advantage that the weld seam can be produced without applying a large amount of material and can be made very thin and exact.

In a further preferred embodiment, before the second tube is connected to the first tube, a lateral bore is formed in the second tube.

This measure is especially advantageous if the space between the first tube and the second tube has only a small height, because forming the lateral bore at a later stage could then cause damage to the first tube. By forming the lateral bore beforehand, such damage to the first tube is reliably avoided.

In a further preferred embodiment, the interconnected unit comprising first tube and second tube is subsequently connected to a connection part for connecting the shaft to a handgrip.

It is further preferred if a longitudinal bore is present in the connection part, or a longitudinal bore is formed in the connection part before connection to the shaft, into which bore the shaft is introduced and then bonded by means of an adhesive.

In this context, it is further preferred if the adhesive used is one which first liquefies under the effect of heat and then cures.

In a further preferred embodiment, before introduction of the adhesive, the lateral bore in the second tube is closed off by means of a subsequently removable stopper.

The advantage of this is that the adhesive, after it has liquefied, cannot penetrate into the space between the outside face of the first tube and the inside face of the second tube.

A further adhesive which cures rapidly and can be removed again is preferably used as stopper.

The use of such an adhesive has the advantage that it can easily be removed again after it has cured and that the lateral bore in the second tube can be closed off particularly quickly, as a result of which the production method can be carried out in a shorter time.

In a further preferred embodiment, a proximal open end of the second tube is closed off before the adhesive is introduced.

The advantage of this is that the adhesive used for connecting the shaft to the connection part is prevented from penetrating into the open proximal end of the second tube. The use of an adhesive which cures quickly, but which in contrast to the aforementioned removable adhesive cannot be removed again, has the advantage that the proximal open end of the space between the inside face of the second tube and the outside face of the first tube can be sealed in a very short time.

In a further preferred embodiment, after the shaft has been bonded adhesively into the connection part, a lateral bore is formed right through the cured adhesive into the first tube at a location not covered by the second tube.

The advantage of this is that the access route to the first tube, formed by the lateral bore, is already sealed off without the need for further sealing measures because the lateral bore is formed through the cured adhesive.

Further advantages and features will become apparent from the following description and from the attached drawing.

BRIEF DESCRIPTION OF THE DRAWINGS

It will be appreciated that the features mentioned above and those still to be explained below can be used not just in the respectively cited combination, but also in other combinations or singly, without departing from the scope of the present invention.

An illustrative embodiment of the invention is shown in the drawing and is described in more detail with reference to said drawing. In the drawings:

FIG. 3 shows a longitudinal section through the upper partial view of the instrument in FIG. 1;

FIG. 4 shows a cross section along the line IV-IV in FIG. 3;

FIG. 6 shows a perspective overall view of the instrument from FIG. 1, with a handgrip represented on a smaller scale than in FIG. 1, said handgrip being shown in a position shortly before locking with the connection part of the shaft.

DETAILED DESCRIPTION OF A PREFERRED EMBODIMENT

Figure 1:
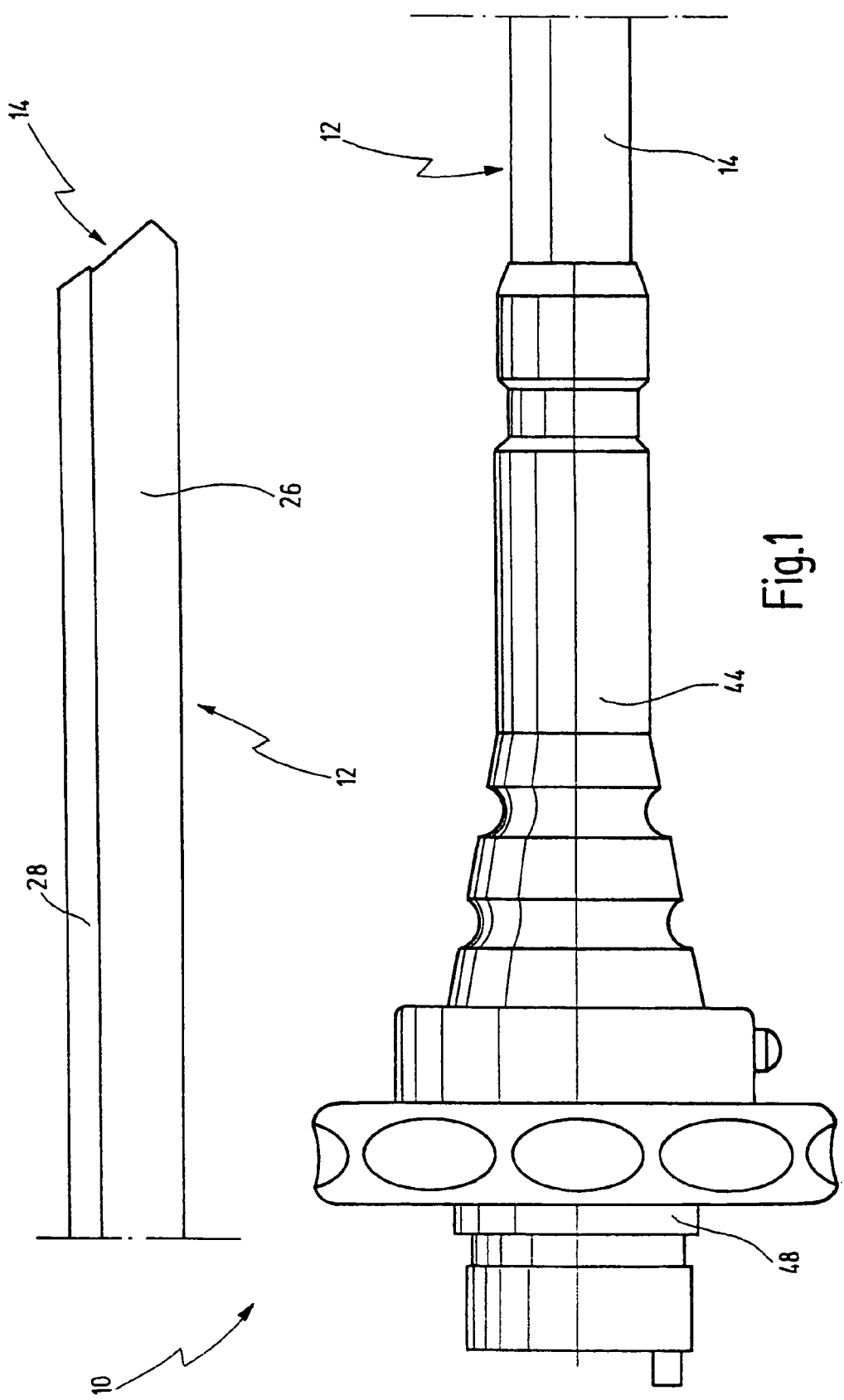
FIG. 1 shows a medical instrument for suction and irrigation in two partial side views.

In FIG. 1, a medical instrument for suction and irrigation is designated overall by reference number 10 and shown in two partial views. The upper partial view in FIG. 1 shows a distal portion of the instrument 10, and the lower partial view shows a proximal portion of the instrument 10 contiguous to the distal portion.

In surgical procedures, particularly in the field of minimally invasive surgery, the instrument 10 is used for delivering irrigation fluid to an operating site and for suctioning fluids and tissue residues from the operating site. The instrument 10 also permits visual monitoring through an endoscope, as will be described below.

Figure 2:
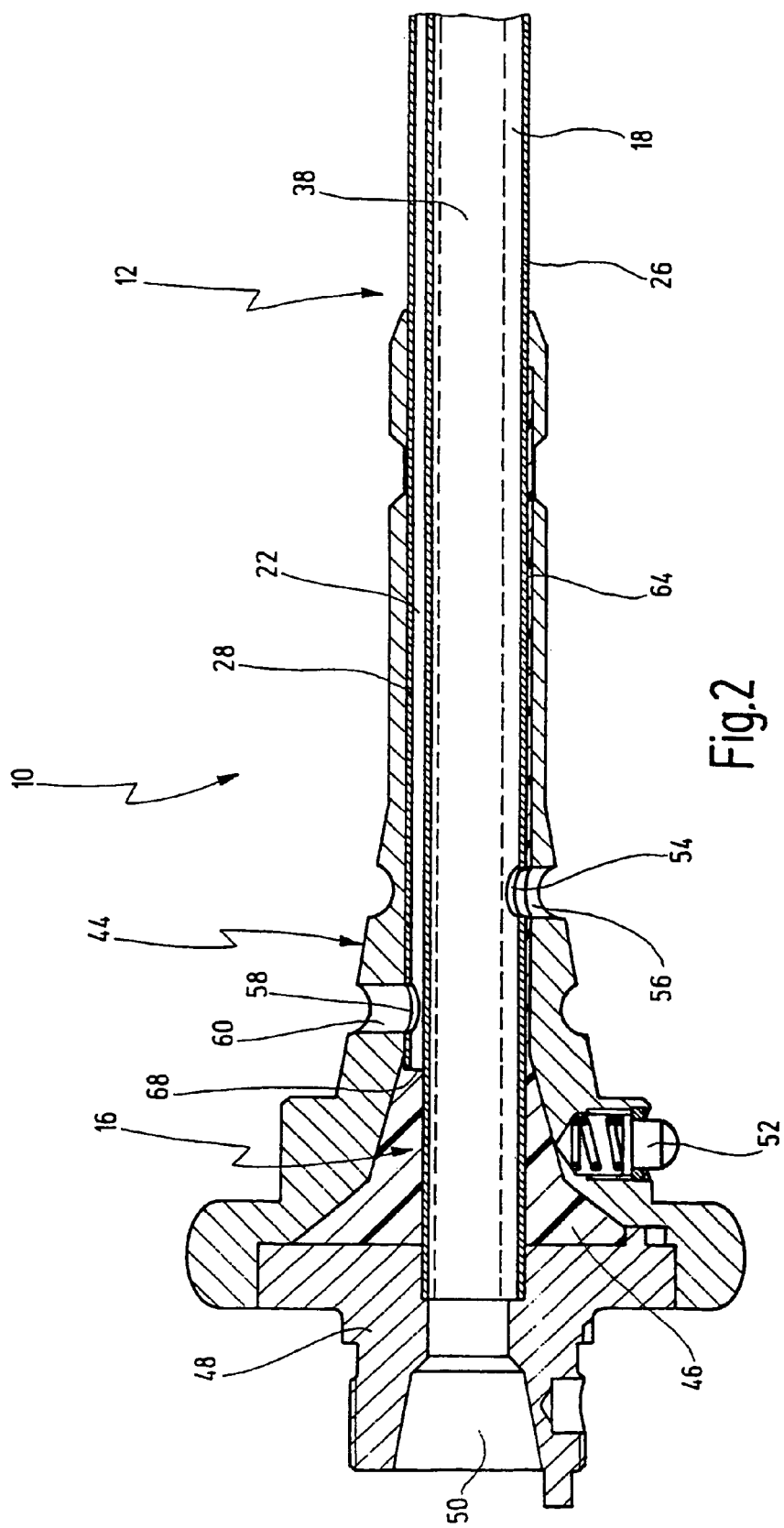
FIG. 2 shows a longitudinal section through the lower partial view of the instrument in FIG. 1.

The instrument 10 has an elongate shaft 12 with a distal end 14 and a proximal end 16 (cf. FIG. 2).

The shaft 12 has a first channel 18 which serves as suction channel and which accordingly has a suction opening 20 at the distal end 14 of the shaft 12.

The shaft 12 also has a second channel 22 which is separate from the first channel 18 and which accordingly has an irrigation opening 24 at the distal end 14 of the shaft 12.

The shaft 12 has a first tube 26 which is closed in cross section (cf. FIG. 4) and in which the first channel 18 (suction channel) is arranged. The shaft 12 also has a second tube 28 which is open in cross section along its length (cf. FIG. 4) and which is placed with its open lengthwise side, here with its lengthwise edges 30 and 32 (cf. FIG. 4), onto an outside face 34 of limited circumference of the first tube 26 and is secured sealingly thereon. The second channel 22 forming the irrigation channel in the shaft 12 is here formed in the space between the outside face 34 of the first tube 26, on which the second tube 28 is placed, and an inside face 36 of the second tube 28.

Along its lengthwise edges 30 and 32, the second tube 28 is sealingly connected to the first tube 26 by a continuous laser weld seam.

According to FIG. 4, the cross section of the first tube 26 is not exactly round, but instead has an oval bulge in its area directed away from the second tube 28. The second tube 28 is formed essentially from a full tube, here a cylinder tube, which has been cut at about the halfway point. The space forming the second channel 22 and arranged between the outside face 34 of the first tube 26 and the inside face 36 of the second tube 28 is designed in the shape of a crescent with low height, so that the overall cross section of the shaft 12 is only slightly greater than the cross section of the first tube 26 on its own. The overall cross section of the shaft 12 is approximately oval, as is indicated in FIG. 4.

The first tube 26 also has a third channel 38 which is indicated by broken lines in FIGS. 2 and 4 and into which an optical shaft (not shown) of an endoscope can be introduced, which then extends as far as the distal end 14 of the shaft 12. The additional channel 38 is not separated from the first channel 18, i.e. the suction channel, by a partition wall.

With an optical shaft inserted into the channel 38, the suction channel 18 is formed by the remaining space between the optical shaft and the first tube 26, as is evident from FIGS. 2 through 4.

The second tube 28 is in this case placed on that outside face 34 of the first tube 26 directed away from the first channel 18 forming the suction channel in the first tube 26. The first channel 18 and the second channel 22 thus lie diametrically opposite one another in relation to the additional channel 38.

As will be seen in particular from FIG. 3, the second tube 28 protrudes slightly beyond the outside face 34 of the first tube 26 on which it is placed. A distal end 40 of the second tube 28, where the irrigation opening 24 is formed, is flanged in toward the first tube 26. Likewise, a distal end 42 of the first tube 26, on the outside face directed away from the second tube 28, is flanged in toward the second tube 28.

A connection part 44 surrounding the shaft 12 and used to connect the shaft 12 to a handgrip 45 shown in FIG. 6 is arranged at the proximal end 16 of the shaft 12 and is fixedly connected to said shaft 12. The fixed connection of the shaft 12 to the connection part 44 is realized by means of a curing adhesive 46 which essentially fills all the spaces between the inside face of the connection part 44 and the outside face of the shaft 12, without penetrating into the interior of the shaft 12, i.e. neither into the channel 22 nor into the channel 18 or channel 38. The adhesive 46 seals the first channel 18 off from the second channel 22 at the proximal end thereof. At its proximal end, the connection part 44 is closed by a cover 48 in which there is a bore 50 for introduction of the endoscope into the channel 38. With the endoscope inserted, this bore 50 is sealed off against the endoscope. According to FIG. 6, the endoscope is introduced into this bore 50 and secured by means of what is known as a ten point coupling 65. The connection part 44 is also provided with a locking knob 52 via which the handgrip 45 can be fixed on the connection part 44.

In the area of the connection part 44, an access point/outlet point is provided both for the first channel 18 forming the suction channel and also for the second channel 22 forming the irrigation channel. For this purpose, in the first tube 26, at its side directed away from the second tube 28, a lateral bore, here a radial bore 54, is present and is in alignment with a bore 56 in the connection part 44. Correspondingly, a bore 58 is present in the second tube 28 and is in alignment with a bore 60 in the connection part 44. The bores 58 and 60 are also radial ones. Provided on the handgrip 45 (FIG. 6) there are corresponding attachments 61, 63 for attaching a suction hose and an irrigation hose. Channels (not shown) extend from these attachments 61, 63 and run through the handgrip 45 and, when the handgrip 45 is placed on the connection part 44, they open out via valves (not shown) into the bores 60 and 56 and thus into the bores 58 and 54. The adhesive 46 seals off the edges of the bores 54 through 60.

With the instrument 10, suction can be obtained permanently through the channel 18, whereas the irrigation via the channel 22 can be switched on at any time via a valve provided on the handgrip (not shown) without the suction via the channel 18 having to be interrupted in order to do this.

A method for production of the instrument 10 is now described in detail below.

In a first step, the first tube 26 and the second tube 28 are formed. The second tube 28 can be produced from a full tube, in this case a cylinder tube, by cutting it open along a half plane so that the second tube 28 has an open lengthwise side. With this open lengthwise side, the second tube 28 is then placed with its lengthwise edges 30 and 32 onto the outside face 34 of the first tube 26 and is fixedly connected to the first tube 26 along the lengthwise edges 30 and 32 by laser welding. In this way, the one-piece shaft 12 is made ready.

Before the second tube 28 is secured on the first tube 26, the lateral bore 58 is formed in the second tube 28.

Figure 5:
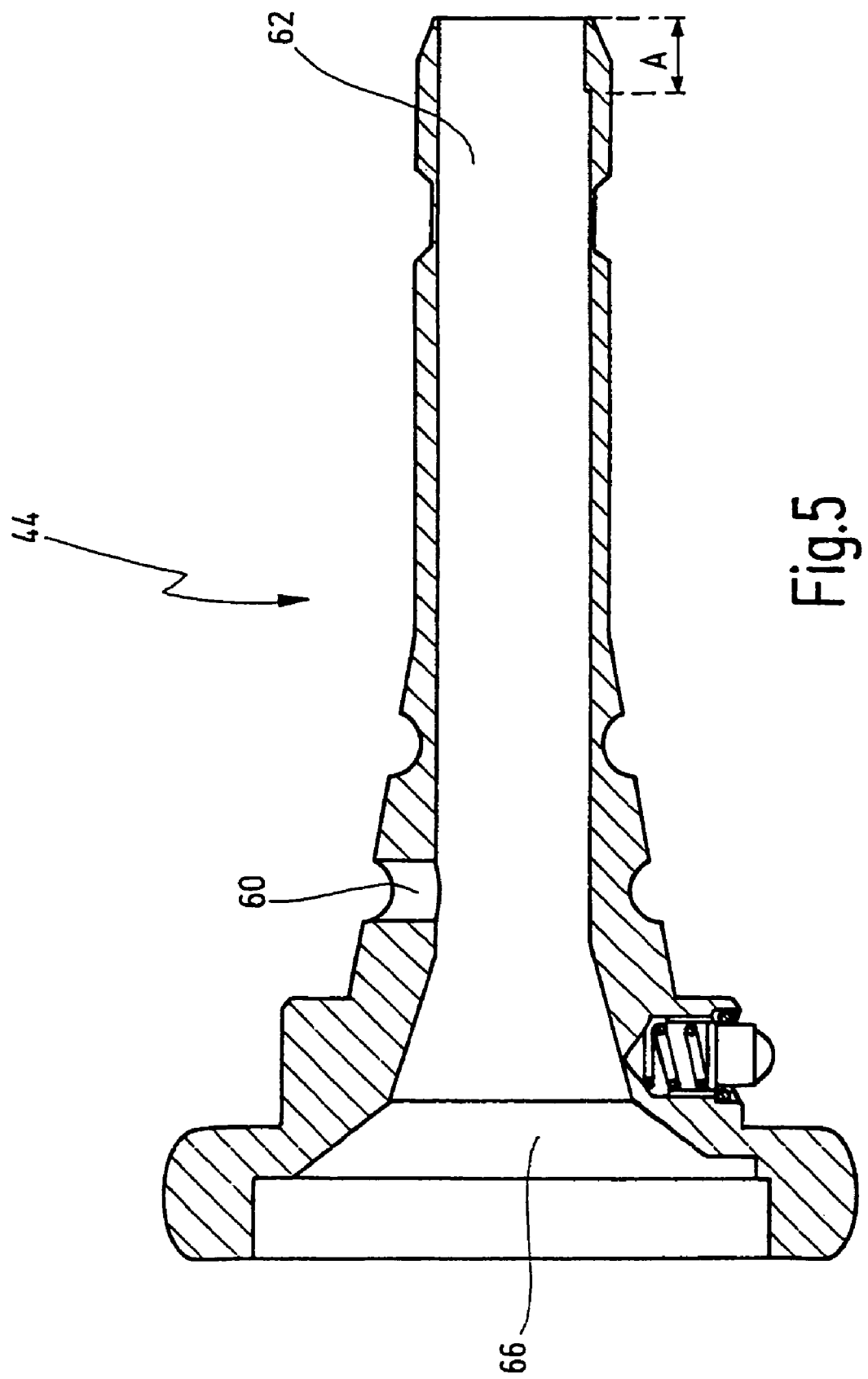
FIG. 5 shows a longitudinal section through part of the instrument from FIG. 1 in isolation.

The interconnected unit composed of first tube 26 and second tube 28 is then connected to the connection part 44. The connection part 44 is made ready in the form shown in FIG. 5. The connection part 44 is a one-piece rotary part in which the lateral bore 60 and a longitudinal bore 62 have first been formed.

After the shaft 12 has been pushed into the connection part 44 to the position shown in FIG. 2, where the bore 58 in the second tube 28 is in alignment with the bore 60 in the connection part 44, introduction of the curing adhesive 46 is then begun. The adhesive 46 is introduced via the open end 66 of the connection part 44 according to FIG. 5, specifically into the space between the proximal end of the shaft 16 and the remaining space of the longitudinal bore 62 in the connection part 44, without adhesive getting into the first tube 26. The adhesive is heated and liquefies, so that the adhesive can flow by a capillary effect into the gap 64 and thus seal off the shaft 12 against the connection part 44.

To prevent a situation where adhesive penetrates into the proximal open end 68 of the second channel 22, this open end 68 is closed off, before introduction of the adhesive 46, by means of a quick-curing additional adhesive which cures within a time. This adhesive then remains at the proximal open end 68 of the second tube 28 after introduction of the adhesive 46.

In order also to prevent a situation where the adhesive 46 penetrates through the bore 58 into the second channel 22, a stopper with an additional adhesive, which likewise cures within a short time, is fitted into the bore 58 before the adhesive 46 is introduced. In this case, an adhesive is used which can be removed again in order to later free the bore 58 as an access to the irrigation channel 22.

Instead of closing the proximal open end 68 and the bore 58, before introduction of the adhesive 46, by means of an additional adhesive, consideration may also be given to introducing the adhesive 46 in several stages into the connection part 44, by which means it is possible to exploit the effect whereby the adhesive initially flows into small gaps, i.e. first positions itself around the edge of the bore 58 and then seals off the edge of the bore 58 from the connection part 44 in the first stage, so that, upon staged introduction of more adhesive 46, no adhesive can flow into the bore 58.

In the first described procedure in which the bore 58 is closed by means of a stopper, it is also preferable for the bore 58 to be formed with a smaller diameter than the bore 60, as this makes it easier to insert the stopper into the bore 58.

After the adhesive 46 has been introduced completely into the connection part 44 and has cured, the bore 56 and the bore 54 are then formed through the adhesive 46 and into the gap 64, so that the bore 54 and the bore 56 are automatically sealed off from the connection part 44. The adhesive 46 seals the first channel 18 off completely from the second channel 22 in the proximal area, so that mixing together of irrigation fluid and suctioned fluid is reliably avoided by the adhesive 46.

In the subsequent stage, the cover 48 is then secured on the connection part 44. The connection part 44 and the shaft 12 including the cover 48 then represent a firmly interconnected one-piece unit.

What is claimed is:

1. A medical instrument for suction and irrigation, comprising an elongate shaft, said shaft having a first tube having a closed wall extending over the full circumference about the longitudinal axis and in which a first channel is present, a second tube having a wall extending over a part of the circumference covering less than the entire circumference about the longitudinal axis of said second tube, said second tube being placed and secured sealingly with said wall extending over a part of the circumference about the longitudinal axis on an outside face of said first tube, thus defining a space between said outside face of said first tube and an inside face of said second tube, said space defining a second channel of said shaft, wherein a connection part surrounding said shaft and used to connect that shaft to a handgrip is arranged at a proximal end of said shaft, said shaft being bonded into said connection part by means of a curing adhesive, wherein said adhesive seals off said first tube and said second tube from one another in a proximal region of said first tube and said second tube, a proximal end of said second tube being closed by means of said adhesive or by means of another adhesive.

2. The instrument of claim 1, wherein said space between said outside face of said first tube and said inside face of said second tube is designed in the shape of a crescent with a low height.

3. The instrument of claim 1, wherein said first tube further has a third channel for receiving an optical shaft of an endoscope, and wherein said second tube is placed on said outside face of said first tube in a location directed away from a remaining free cross section in said first tube which forms said first channel.

4. The instrument of claim 1, wherein said second tube protrudes slightly in longitudinal direction beyond said outside face of said first tube.

5. The instrument of claim 1, wherein a distal end of said second tube is flanged in toward said first tube.

6. The instrument of claim 1, wherein a distal end of said first tube, in a location of said outside face directed away from said second tube, is flanged in toward said second tube.

7. The instrument of claim 1, wherein said first channel is a suction channel and said second channel is an irrigation channel.

8. The instrument of claim 1, wherein said second tube is fixedly connected to said outside face of said first tube by at least one of adhesive bonding, soldering, welding.

9. The instrument of claim 1, wherein said second tube is connected to said outside face of said first tube by laser welding.

10. A method for producing a medical instrument for suction and irrigation, comprising providing a first tube having a closed wall extending over the full circumference about the longitudinal axis and in which a first channel is present, providing a second tube having a wall extending over a part of the circumference covering less than the entire circumference about the longitudinal axis of said second tube, placing and securing sealingly said second tube with said wall extending over a part of the circumference about the longitudinal axis on an outside face of said first tube to form a shaft, and thus defining a space between said outside face of said first tube and an inside face of said second tube, said space defining a second channel of said shaft, connecting said first tube and said second tube after having been connected with one another to a connection part for connecting said shaft to a handgrip, introducing said shaft into a longitudinal bore in said connection part and bonding said shaft to said connection part by means of an adhesive, said adhesive sealing off the first tube and the second tube from one another in a proximal region of said first tube and said second tube, a proximal end of said second tube being closed by means of said adhesive or by means of another adhesive.

11. The method of claim 10, further comprising fixedly connecting said second tube to said first tube by at least one of adhesive bonding, soldering, welding.

12. The method of claim 10, further comprising connecting said second tube to said first tube by laser welding.

13. The method of claim 10, further comprising forming a lateral bore in said second tube prior to connecting said second tube to said first tube.

14. The method of claim 10, wherein said adhesive used is one which first liquefies under heat and than cures.

15. The method of claim 13, further comprising closing off said lateral bore in said second tube by means of a subsequently removable stopper.

16. The method of claim 15, wherein an adhesive, which cures rapidly and which can be removed again is used as said removable stopper.

17. The method of claim 10, further comprising forming a lateral bore through said cured adhesive into said first tube at a location not covered by said second tube, after said shaft having being bonded adhesively into said connection part.

* * * * *